(12) United States Patent
Ticehurst

(10) Patent No.: US 9,719,368 B2
(45) Date of Patent: Aug. 1, 2017

(54) METHOD OF INSPECTING THE FAN TRACK LINER OF A GAS TURBINE ENGINE

(71) Applicant: ROLLS-ROYCE PLC, London (GB)

(72) Inventor: Michael David Ticehurst, Lincoln (GB)

(73) Assignee: ROLLS-ROYCE plc, London (GB)

( * ) Notice: Subject to any disclaimer, the term of this patent is extended or adjusted under 35 U.S.C. 154(b) by 183 days.

(21) Appl. No.: 14/593,606

(22) Filed: Jan. 9, 2015

(65) Prior Publication Data

US 2015/0204210 A1    Jul. 23, 2015

(30) Foreign Application Priority Data

Jan. 23, 2014    (GB) .................................. 1401111.8

(51) Int. Cl.
*G01N 29/265*    (2006.01)
*G01N 29/26*    (2006.01)
(Continued)

(52) U.S. Cl.
CPC ........... *F01D 21/003* (2013.01); *G01M 15/14* (2013.01); *G01N 29/043* (2013.01);
(Continued)

(58) Field of Classification Search
CPC .. G01N 29/226; G01N 29/265; G01N 29/285; G01N 29/225; G01N 29/043;
(Continued)

(56) References Cited

U.S. PATENT DOCUMENTS 4,395,827 A * 8/1983 Stowe .................... F01D 11/08
33/613
4,659,988 A * 4/1987 Goff ........................ G01B 7/14
324/207.25
(Continued)

FOREIGN PATENT DOCUMENTS

EP    2570676 A2    3/2013
FR    2 973 110 A1    9/2012
(Continued)

OTHER PUBLICATIONS

Jun. 11, 2015 European Search Report issued in Application No. 15150589.8.
(Continued)

*Primary Examiner* — Helen Kwok
(74) *Attorney, Agent, or Firm* — Oliff PLC

(57) ABSTRACT

A method of inspecting the fan track liner of a gas turbine engine of a type having a rotatable propulsive fan circumscribed by a fan track liner and having a plurality of fan blades extending radially outwardly from a central hub. The method comprises the steps of: affixing at least part of an inspecting device to the fan so as to be directed towards the fan track liner; and rotating the fan within the fan track liner to move the at least part of the inspecting device circumferentially relative to at least a region of the fan track liner to thereby scan the region of the fan track liner with the at least part of the inspecting device.

15 Claims, 5 Drawing Sheets

(51) Int. Cl.
*G01N 29/24* (2006.01)
*F01D 21/00* (2006.01)
*G01N 29/22* (2006.01)
*G01N 29/04* (2006.01)
*G01N 29/28* (2006.01)
*G01M 15/14* (2006.01)

(52) U.S. Cl.
CPC ......... *G01N 29/225* (2013.01); *G01N 29/226* (2013.01); *G01N 29/265* (2013.01); *G01N 29/28* (2013.01); *F05D 2260/80* (2013.01); *F05D 2260/83* (2013.01); *F05D 2270/806* (2013.01); *G01N 2291/2693* (2013.01)

(58) Field of Classification Search
CPC ..... F01D 21/003; G01M 15/14; G01M 15/02; G01B 21/16
USPC .............. 73/634, 640, 618, 633, 635, 112.01
See application file for complete search history.

(56) References Cited

U.S. PATENT DOCUMENTS

| | | | |
|---|---|---|---|
| 5,627,761 A * | 5/1997 | Pollard | G01B 7/14 324/207.22 |
| 5,781,007 A * | 7/1998 | Partika | G01N 27/9013 324/220 |
| 6,532,840 B2 * | 3/2003 | Hatley | B25J 5/00 356/241.1 |
| 7,313,961 B2 * | 1/2008 | Tenley | G01N 29/226 73/634 |
| 7,579,844 B2 * | 8/2009 | Ducheminsky | G01B 7/14 324/622 |
| 7,916,311 B2 * | 3/2011 | Corn | G01B 11/14 356/614 |
| 8,102,539 B2 * | 1/2012 | Ghulam | G01B 11/14 356/614 |
| 9,068,906 B2 * | 6/2015 | Silieti | G01M 15/02 |
| 2005/0126291 A1 * | 6/2005 | Czerw | G01N 29/265 73/589 |
| 2007/0089545 A1 * | 4/2007 | Roney | F01D 21/003 73/865.8 |
| 2007/0157733 A1 * | 7/2007 | Litzenberg | G01N 29/043 73/644 |
| 2007/0272042 A1 * | 11/2007 | Goldfine | G01B 7/285 73/865.8 |
| 2008/0218181 A1 | 9/2008 | Ducheminsky et al. | |
| 2008/0245151 A1 * | 10/2008 | Roney | F01D 25/285 73/628 |
| 2011/0029282 A1 | 2/2011 | Berkcan et al. | |
| 2016/0195411 A1 * | 7/2016 | Ford | F01D 17/02 415/118 |

FOREIGN PATENT DOCUMENTS

| | | |
|---|---|---|
| GB | 2462829 A | 2/2010 |
| GB | 2471465 A | 1/2011 |

OTHER PUBLICATIONS

Jul. 2, 2014 Search Report Issued in British Application No. 1401111.8.

* cited by examiner

METHOD OF INSPECTING THE FAN TRACK LINER OF A GAS TURBINE ENGINE

The present invention relates to a method of inspecting the fan track liner of a gas turbine engine, and more particularly relates to such a method performed on an engine of a type having a rotatable propulsive fan circumscribed by a fan track liner and having a plurality of fan blades extending radially outwardly from a central hub.

BACKGROUND

Gas turbine engines of the so-called ducted-fan type are well known and widely used for powering aircraft, and commercial aircraft in particular. Engines of this type have a relatively large propulsive fan comprising a plurality of generally radial fan blades and which is mounted for rotation about the principle rotational axis of the engine within a nacelle comprising a fan case. The principle functions of the fan case include; defining the outer annulus of the gas flow through the engine and containment of a fan blade should it disintegrate or become detached from the fan during flight. The fan case thus includes a fan track liner which circumscribes the fan, and which is configured to absorb the energy of a detached fan blade to prevent the blade passing through the core of the engine. The radially innermost surface of the fan track liner is typically provided in very close proximity to the outer tips of the fan blades in order to maintain an effective seal across the fan, for reasons of engine efficiency and performance. This is usually achieved by configuring the fan track liner so that it is abradable by the tips of the blades to maintain tight blade tip clearances.

As will be appreciated, given the importance of the requirement for the fan track liner to absorb the energy of a detached fan blade, the integrity of the liner is very important. It is thus considered important to check and monitor the integrity of the fan track liner during the service life of an engine. Current methods and techniques for inspecting the integrity of the fan track liner during service are considered to be less than optimal in terms of efficiency and convenience. For example, it is common for inspection of an engine's fan track liner to require complete removal of the fan from the engine in order to provide sufficient access to the fan track liner.

SUMMARY OF INVENTION

It is an object of the present invention to provide an improved method of inspecting the fan track liner of a gas turbine engine.

According to a first aspect of the present invention, there is provided a method of inspecting the fan track liner of a gas turbine engine of a type having a rotatable propulsive fan circumscribed by a fan track liner and having a plurality of fan blades extending radially outwardly from a central hub, the method comprising the steps of: affixing at least part of an inspecting device to the fan so as to be directed towards the fan track liner; and rotating the fan within the fan track liner to move said at least part of the inspecting device circumferentially relative to at least a region of the fan track liner to thereby scan said region of the fan track liner with said at least part of the inspecting device.

The method may be performed without removing the fan from the engine such that said step of rotating the fan is performed with the fan in its normal position within the engine. Said step of rotating the fan can be performed manually by hand.

The method may be performed such that said step of rotating the fan involves rotating the fan through at least 360 degrees to thereby scan the entire circumference of at least a region of the fan track liner with said at least part of the inspecting device.

The method may further include the steps of: adjusting the axial position of said at least part of the inspecting device affixed to the fan relative to said fan track liner after said step of rotating the fan, and then repeating said step of rotating the fan to move said at least part of the inspecting device circumferentially relative to a further region of the fan track liner, thereby scanning said further region of the fan track liner with said at least part of the inspecting device.

Said steps of adjusting the axial position of said at least part of the inspecting device affixed to the fan relative to said fan track liner, and rotating the fan may be repeated a plurality of times to scan the fan track liner in a plurality of axial increments.

Said step of affixing at least part of the inspecting device to the fan may involve positioning said at least part of the inspecting device adjacent the fan track liner, such that said step of rotating the fan is effective to move said at least part of the inspecting device across the radially innermost surface of the fan track liner.

The method may include the steps of: removing a fan blade from the fan; and replacing said removed fan blade with a support extending radially outwardly from the hub of the fan and which supports said at least part of the inspecting device adjacent the fan track liner.

Only a single said fan blade may be removed from the fan.

Advantageously, said support may be provided in the form of a designated test-blade of similar form to the fan blades of the fan. The test-blade may be shorter in the radial direction than the fan blades forming the fan, and may have an assembly comprising said at least part of the inspecting device mounted to its radially outermost region.

Said inspecting device may be configured to identify anomalies in the structure of the fan track liner.

Said inspecting device may comprise first and second elements, at least one of said elements being affixed to the fan. The first element may be a receiver and the second element may be an emitter.

The inspecting device may comprise a transducer, such as an ultrasonic transducer which is affixed to said fan.

The transducer may be provided within an assembly which, when affixed to the fan, is supported in sliding contact with the radially innermost surface of the fan track liner during the or each said step of rotating the fan.

Optionally, said assembly is supported for axial movement relative to said support.

Optionally, said assembly is radially outwardly biased towards the fan track liner.

Said assembly may comprise an ultrasonic couplant material arranged between the ultrasonic transducer and the fan track liner and for sliding contact with the fan track liner during the or each said step of rotating the fan to facilitate the transmission of ultrasonic energy from the transducer into the fan track liner.

The couplant material may be resilient.

The method may comprise the step of directing an ultrasonic couplant liquid between the transducer and the fan track liner during the or each step of rotating the fan. Water can be used as the couplant liquid.

The couplant liquid may be directed between said couplant material and the fan track liner during the or each step of rotating the fan.

Optionally, the method may further include the step of collecting excess couplant liquid from between the transducer and the fan track liner via the localised application of a vacuum during the or each step of rotating the fan.

According to a second aspect of the present invention, there is provided a method of inspecting the fan track liner of a gas turbine engine of a type having a rotatable propulsive fan circumscribed by a fan track liner and having a plurality of fan blades extending radially outwardly from a central hub, the method comprising the steps of: removing a fan blade from the fan; replacing said removed fan blade with a support extending radially outwardly from the hub of the fan and which supports an ultrasonic transducer adjacent the fan track liner; rotating the fan about its rotational axis to move the transducer circumferentially across at least a region of the radially innermost surface of the fan track and thereby scanning at least said region of the fan track liner with the transducer.

The method of the second aspect is preferably performed without removing the fan from the engine such that said step of rotating the fan is performed with the fan in its normal position within the engine. The step of rotating the fan may be performed manually by hand.

Only a single said fan blade may be removed from the fan during the method of the second aspect.

In the method of the second aspect said support may be provided in the form of a designated test-blade of similar form to the fan blades of the fan.

Said test-blade may be shorter in the radial direction than the fan blades forming the fan, and may have an assembly comprising said transducer mounted to its radially outermost region.

Said step of rotating the fan may involve rotating the fan through at least 360 degrees to thereby scan the entire circumference of at least a region of the fan track liner with the transducer.

The method of the second aspect optionally includes the steps of: adjusting the axial position of the transducer relative to said fan track liner after said step of rotating the fan, and then repeating said step of rotating the fan to move the transducer circumferentially across another region of the radially innermost surface of the fan track, thereby scanning said further region of the fan track liner with the transducer.

Said steps of adjusting the axial position of the transducer relative to said fan track liner and rotating the fan may be repeated a plurality of times to scan the fan track liner in a plurality of axial increments.

The transducer may be provided within an assembly which is supported by said support in sliding contact with the radially innermost surface of the fan track liner during the or each said step of rotating the fan.

Said assembly may be supported for axial movement relative to said support, and is optionally outwardly biased towards the fan track liner.

Advantageously, said assembly comprises an ultrasonic couplant material arranged between the ultrasonic transducer and the fan track liner and for sliding contact with the fan track liner during the or each said step of rotating the fan to facilitate the transmission of ultrasonic energy from the transducer into the fan track liner. Said couplant material may be resilient.

The method of the second aspect may further comprise the step of directing an ultrasonic couplant liquid between the transducer and the fan track liner during the or each step of rotating the fan. The couplant liquid may be water and is preferably directed between said couplant material and the fan track liner during the or each step of rotating the fan.

The method optionally further includes the step of collecting excess couplant liquid from between the transducer and the fan track liner via the localised application of a vacuum during the or each step of rotating the fan.

The method of either the first aspect, or the second aspect, outlined above may be performed on an engine which is mounted to an aircraft, and without removal of the engine from the aircraft.

DESCRIPTION OF THE DRAWINGS

So that the invention may be more readily understood, and so that further features thereof may be appreciated, embodiments of the invention will now be described by way of example with reference to the accompanying drawings in which.

DETAILED DESCRIPTION

Figure 1:
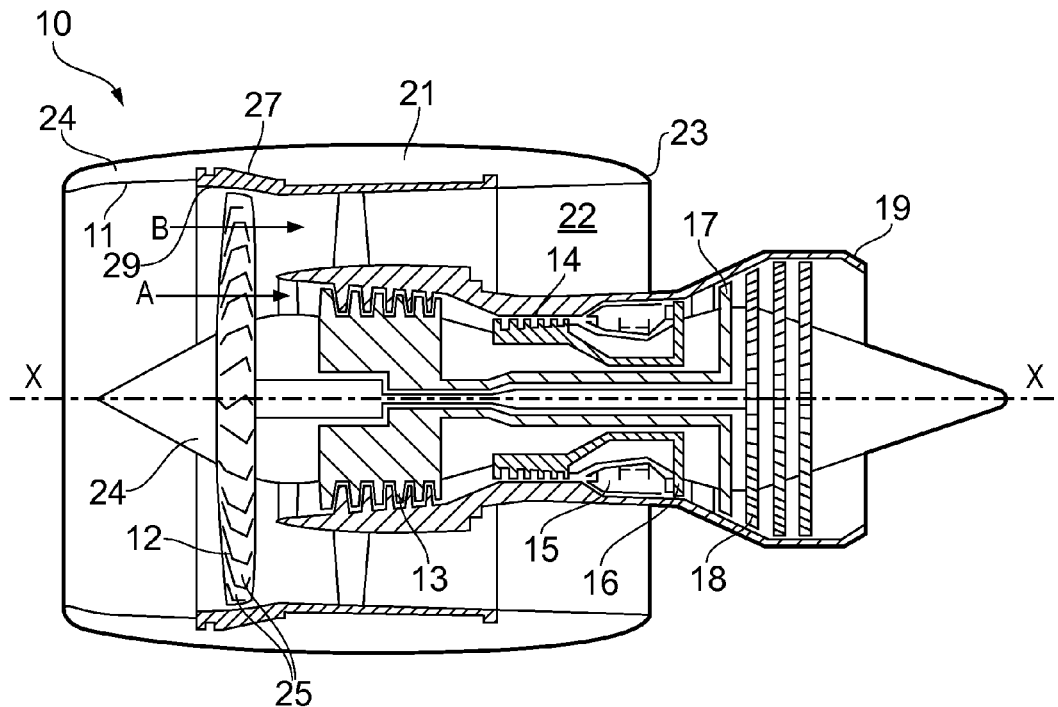
FIG. 1 is a schematic longitudinal cross-sectional view through a gas turbine engine.

Turning now to consider the drawings in more detail, FIG. 1 shows ducted fan gas turbine engine, generally indicated at 10, of a type on which the method of the present disclosure may be practiced. The engine has a principal and rotational axis X-X and comprises, in axial flow series, an air intake 11, a propulsive fan 12, an intermediate pressure compressor 13, a high-pressure compressor 14, combustion equipment 15, a high-pressure turbine 16, an intermediate pressure turbine 17, a low-pressure turbine 18 and a core engine exhaust nozzle 19. A nacelle 21 generally surrounds the engine 10 and defines the intake 11, a bypass duct 22 and a bypass exhaust nozzle 23.

During operation, air entering the intake 11 is accelerated by the fan 12 to produce two air flows: a first air flow A into the intermediate pressure compressor 13 and a second air flow B which passes through the bypass duct 22 to provide propulsive thrust. The intermediate pressure compressor 13 compresses the air flow A directed into it before delivering that air to the high pressure compressor 14 where further compression takes place.

The compressed air exhausted from the high-pressure compressor 14 is directed into the combustion equipment 15 where it is mixed with fuel and the mixture combusted. The resultant hot combustion products then expand through, and thereby drive, the high, intermediate and low-pressure turbines 16, 17, 18 before being exhausted through the nozzle 19 to provide additional propulsive thrust. The high, intermediate and low-pressure turbines respectively drive the high and intermediate pressure compressors 14, 13 and the fan 12 by respective coaxial interconnecting shafts.

Figure 2:
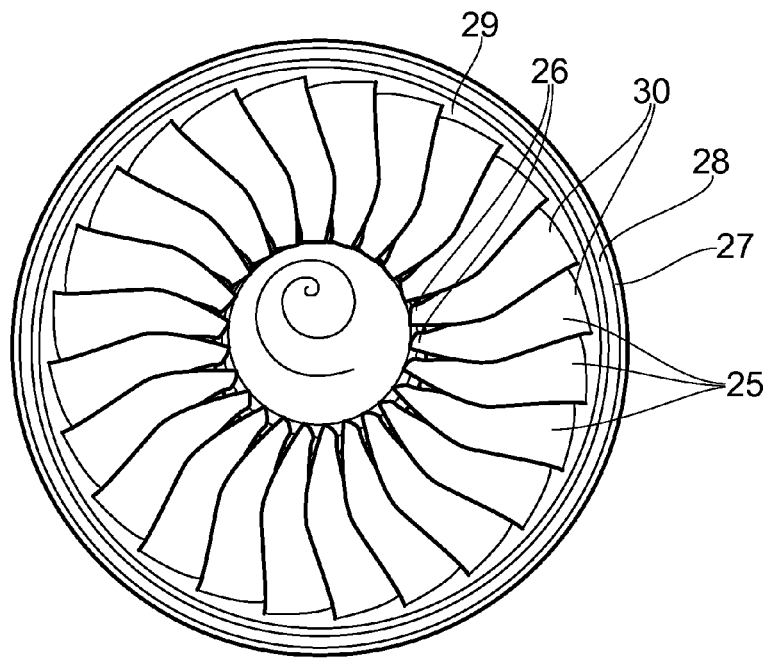
FIG. 2 is an elevational view of the engine from the front.

The fan 12 comprises a central hub 24 to which a plurality of generally radially extending aerofoil-shaped fan blades 25 are mounted at their root regions 26 as shown most clearly in FIG. 2 which shows the engine as viewed from the front but with the outer cowling of the nacelle 21 removed. As is conventional, the root regions 26 of the blades 25 are configured to be slideably received and locked within respective mounting slots formed in the hub 24. The mounting slots are parallel with the rotational axis X-X of the engine and so the blades 25 can each be separately removed from the fan 12 in a forwards direction for servicing and maintenance without requiring complete removal of the fan 12 from the engine 10.

Within the forward part of the nacelle 21, there is provided a fan case 27 which extends around the fan 12. The fan case 27 is provided with a fan track liner which circumscribes the fan 12 such that the radially innermost surface 29 of the fan track liner 28 is in close proximity, or rubbing contact, with the radially outermost tips 30 of the fan blades as illustrated in FIG. 2. As explained hereinbefore, the fan track liner 28 is configured to absorb the energy of a detached fan blade 25 and also to provide an effective seal between the rotating fan 12 and the fan case 27. It is therefore important to inspect the structural integrity of the fan track liner 28 regularly during the service life of the engine.

The present disclosure proposes a convenient method of inspecting the fan track liner 28 of the engine 10, which can be performed without removal of the fan 12 from the engine 10. In its broadest sense, the present disclsoure proposes a method which involves affixing at least part of an inspecting device (such as an ultrasonic transducer in some embodiments) to the fan 12, in a position and orientation such that it is directed towards the fan track liner 28. The fan 12 is then rotated, which may be done manually by hand, within the fan track liner 28 so as to move the affixed part of the inspecting device circumferentially relative to the fan track liner 28 to thereby scan at least a region of the fan track liner 28 with the device.

Figure 3:
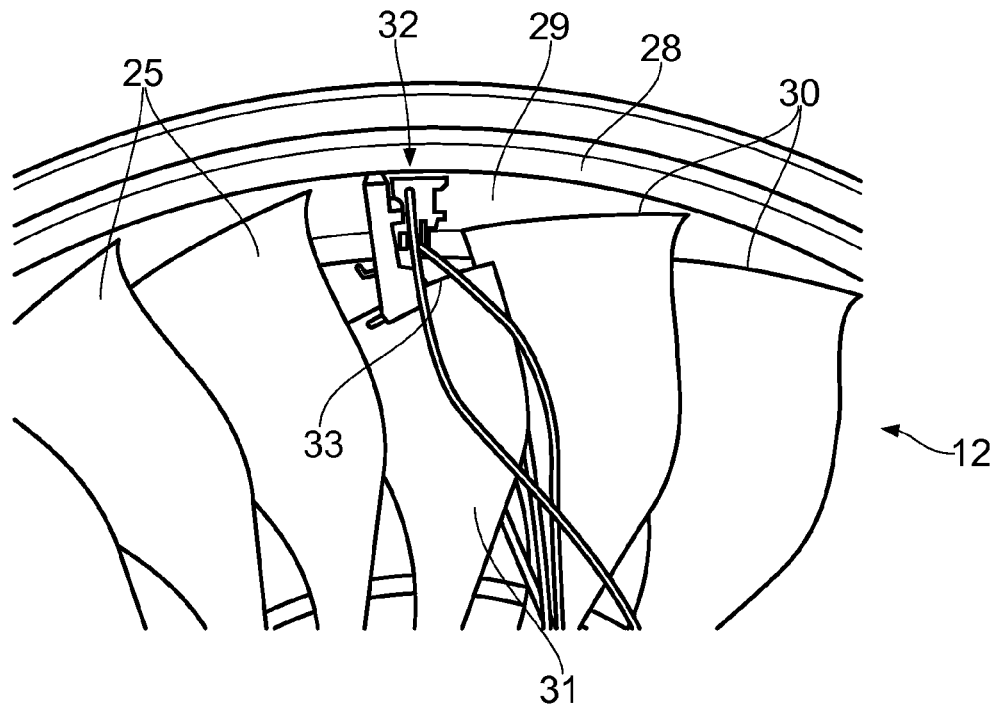
FIG. 3 is shows a peripheral region of the engine's propulsive fan and fan track liner, with one of the fan's blades replaced with a test-blade.

FIG. 3 illustrates this basic principle with reference to a specific embodiment of the present disclosure which involves the removal of one of the fan's blades 25, but which doesn't require complete removal of the fan 12 from the engine 10. More particularly, FIG. 3 shows a region of the fan 12 and the fan track liner 28 during inspection, but after removal of one of the fan's blades 25 by detaching it from the hub of the fan in the manner described above. The removed blade has been replaced with a designated test-blade 31 which acts as a support for a testing assembly 32.

The test-blade 31 may have a substantially identical form to the fan's normal blades 25, particularly in its root region (not shown in FIG. 3) and along its length, so that the test blade 31 may be mounted to the hub of the fan in the same manner as the normal fan blades 25. When mounted to the hub of the fan 12 in this manner the test-blade 31 extends generally radially outwardly from the hub in the same manner as the fan's normal blades 25, as clearly shown in FIG. 3.

However, at its radially outermost region, the test-blade 31 differs from the fan's normal blades 25. Specifically, it will be noted that the test-blade is somewhat shorter in the radial direction than the normal blades 25. This can simply be achieved by cutting down a spare blade of the type used in the fan 12. The shorter radial length of the test blade 31 provides a larger space between the tip 33 of the test blade 31 and the radially innermost surface 29 of the fan track liner 28. This space accommodates the testing assembly 32, which is mounted to the tip region of the test-blade 31 in a position in which part of the assembly lies against the inner surface 29 of the fan track liner 28.

Figure 4:
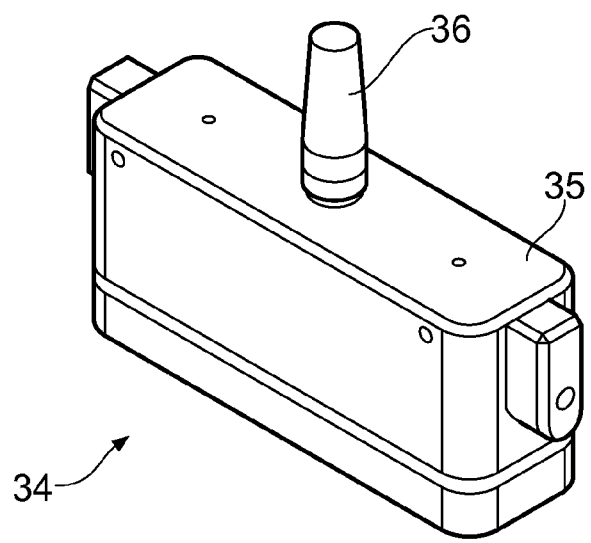
FIG. 4 is a schematic perspective view showing an ultrasonic transducer suitable for use in the method of the present disclosure.

FIG. 4 illustrates an ultrasonic transducer probe 34, of a type known per se, which is used as the inspecting device in the illustrated embodiment and which forms part of the testing assembly 32. Of course it should be appreciated that transducers operating at frequencies outside the ultrasonic range could be used instead. The transducer probe 34 comprises a housing 35 and has an electrical connector 36 to which a cable can be connected for operation of the transducer.

Figure 5:
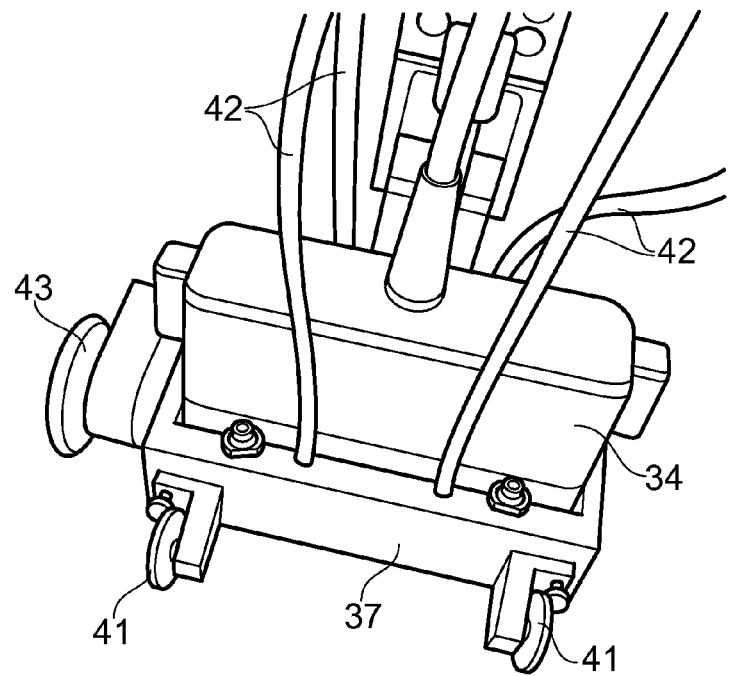
FIG. 5 is a perspective view showing part of a test assembly comprising the transducer of FIG. 4.
Figure 6:
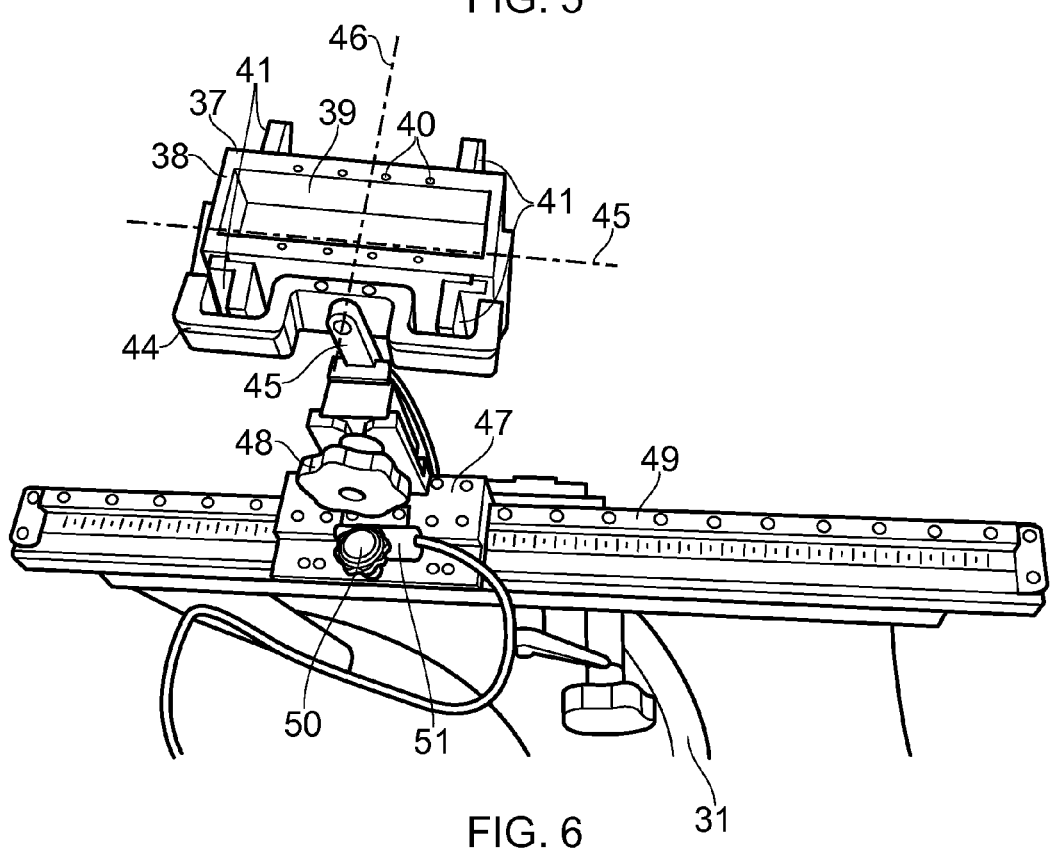
FIG. 6 shows the test assembly of FIG. 5 mounted to the end of the test-blade.

As shown in more detail in FIGS. 5 and 6, the transducer probe 34 is mounted within a chassis 37 which forms part of the testing assembly 32 mounted to the end of the test-blade 31. The chassis 37 is configured so as to have an opening 38, which in the embodiment illustrated is substantially rectangular, towards which the emitting/receiving region of the transducer probe 34 is directed. The opening 38 is filled with a block of resilient couplant material 39 which is arranged in abutment with the emitting/receiving region of the transducer probe 34. The couplant material 39 is selected to allow transmission therethrough of the energy emitted by the transducer 39 during operation, and defines a substantially smooth and planar outer surface which, as illustrated in FIG. 6, is generally flush with the edges of the opening 38.

A series of small outlet ports 40 are provided in the chassis 37, adjacent the edges of the opening 38 and the couplant material 39 therein. The outlet ports 40 are fluidly connected to a supply of couplant liquid by a series of pipes 42 as illustrated in FIG. 5. As will be explained in more detail, a suitable couplant liquid, such as water, is pumped through the pipes 42 during operation of the testing assembly, so as to flow outwardly from the outlet ports 40. The material velocity of the couplant material 39 to the frequency range of energy emitted by the transducer probe 34 is preferably matched to the material velocity of water to the same frequency range.

FIG. 5 shows the chassis 37 adjacent the fan track liner of an engine such that the outer surface of the couplant material 39 is urged against, or at least into intimately close relationship with, the radially innermost surface 29 of the fan track liner. As will be appreciated, in this operative position the couplant material 39 serves to space the transducer probe from the inner surface 29 of the fan track liner. The block of couplant material has a thickness (for example approximately 25 mm) which is effective to space the probe 34 sufficiently from the fan track liner for the fan track liner to fall within the far field region of the energy beam emitted by the transducer probe during operation. Furthermore, the block of couplant material 39 serves to couple the probe to the inner surface 29 of the fan track liner, which coupling can be further improved by flowing a thin film of the couplant liquid through the outlet ports 40 and thus between the couplant material 39 and the fan track liner.

Small guide wheels 41 are freely rotatably mounted to the chassis 34 so as to contact the inner surface 29 of the fan track liner, and thereby guide the chassis 37 in a sliding manner across the inner surface 29 of the fan track liner during use, as will be explained in more detail below. Additionally, the chassis 37 is provided with an encoder wheel 44 which is arranged to be resiliently biased against the inner surface 29 of the fan track liner and which is associated with a digital encoder configured to track and record movement of the chassis 37 across the fan track liner.

As shown most clearly in FIG. 6, the chassis 37 is pivotally mounted to a gimbal bracket 44 for pivotal movement relative to the bracket about a first pivot axis 45. The bracket 44, in turn, is pivotally mounted to a support post 45 for pivotal movement relative to the post about a second pivot axis 46. The first and second pivot axes are orthogonal.

The support post 45 is slideably engaged in a corresponding track on a slide carriage 47. Coarse adjustment of the position of the post 45 within the track on the carriage 47 is provided by a knob 48 which is operable to engage and disengage a pin in selected holes along the support post. Additionally, however, the support post is resiliently biased away from the slide carriage, for example via a spring arrangement (not shown).

The slide carriage 47 is slideably mounted to an elongate slide track 49 which in turn is mounted to the radially outermost end of the test-blade 31. In the arrangement illustrated in FIG. 6, the longitudinal axis of the slide track 49 is substantially aligned with the first pivot axis 45 about which the chassis 37 is pivotable relative to the gimbal bracket 44.

The slide carriage 47 can be moved slideably along the slide track 49 to any desired position and then locked in that position, for example via a clamp arrangement operable via a knob 50. Additionally, the slide carriage 47 includes a second encoder 51 which is arranged and configured to record the position of the carriage 47 relative to the slide track 49.

In order to inspect the fan track liner 28 of the engine 10, a fan blade 25 is initially removed from the fan 12 and replaced by the test-blade 31 as already described above. The test assembly 32 may then be mounted to the end of the test blade 31 such that the longitudinal axis of the slide track 49 is substantially parallel to the rotational axis X-X of the engine. The axial position of the slide carriage (and hence also the chassis 37 carrying the transducer probe 34) relative to the slide track 49 is then set in dependence on the axial extent of the fan track liner which is to be inspected. The radial spacing between the chassis 37 and the slide carriage 47 may then be adjusted via operation of the first knob 48, and relative movement of the support post 45 and the carriage 47 to bring the outer surface of the couplant material 39 into close facing relationship with the inner surface 29 of the fan track liner, with its guide wheels 41 and encoder wheel 43 making rolling contact with the inner surface 29 of the fan track liner 28.

Figure 7:
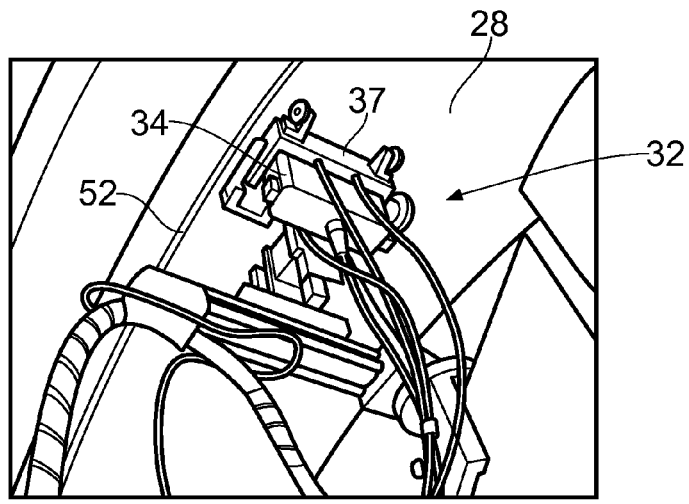
FIG. 7 shows the test assembly mounted to the end of the test-blade in use during the method of the present disclosure to scan an initial region of the engine's fan track liner.

FIG. 7 shows the testing assembly positioned as described above such that the chassis 37 is adjacent the forward edge 52 of the fan track liner 28. The transducer probe 34 and the encoders 43, 51 are connected to a controlling computer (not shown) to control energy emission by the transducer probe 34, the recordal of energy received by the transducer probe 34, and the position of the probe 34 relative to the fan track liner 28.

With the testing assembly 32 positioned and adjusted as described above, the fan 12 of the engine is then rotated in its normal position within the fan track liner 28 to move the chassis 37 across the inner surface 29 of the fan track liner 28 whilst directing a flow of the couplant liquid between the couplant material 38 and the fan track liner via the outlet ports 40. It is envisaged that the fan will be rotated manually by hand for this purpose, and typically through approximately 370° (or at least 360°) such that the transducer probe 34 is scanned across the full circumference of the fan track liner 28 in order to provide data (recorded by the computer together with the position of the probe 34) representative of the integrity of the fan track liner around its entire circumference.

Figure 8:
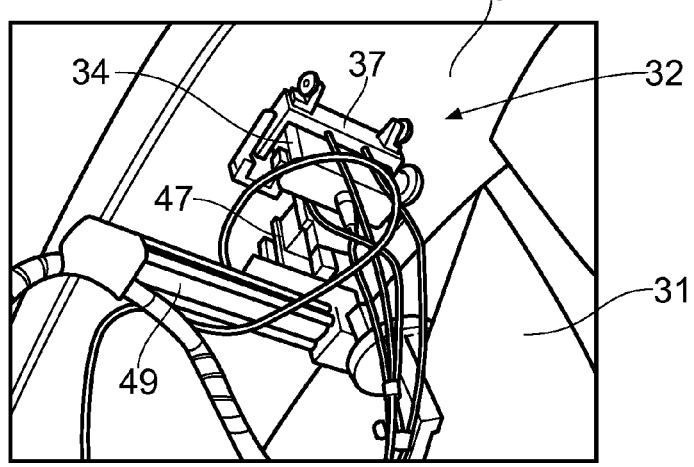
FIG. 8 is a view corresponding generally to that of FIG. 7, but which shows part of the test assembly in an alternate position relative to the fan track liner during scanning of another region of the fan track liner.
Figure 9:
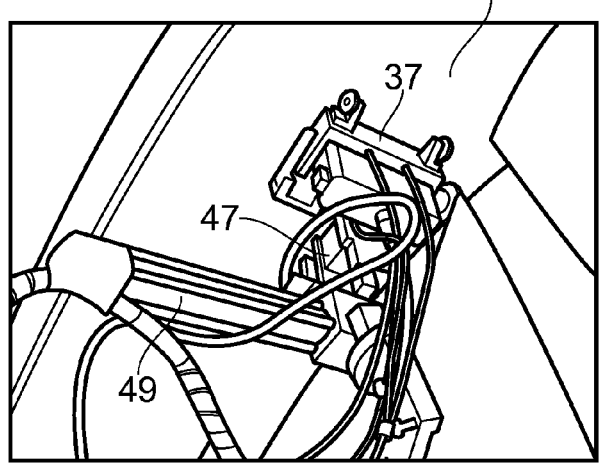
FIG. 9 is a view corresponding generally to that of FIG. 8, showing part of the test assembly in another alternate position relative to the fan track liner during scanning of a further region of the fan track liner.
Figure 10:
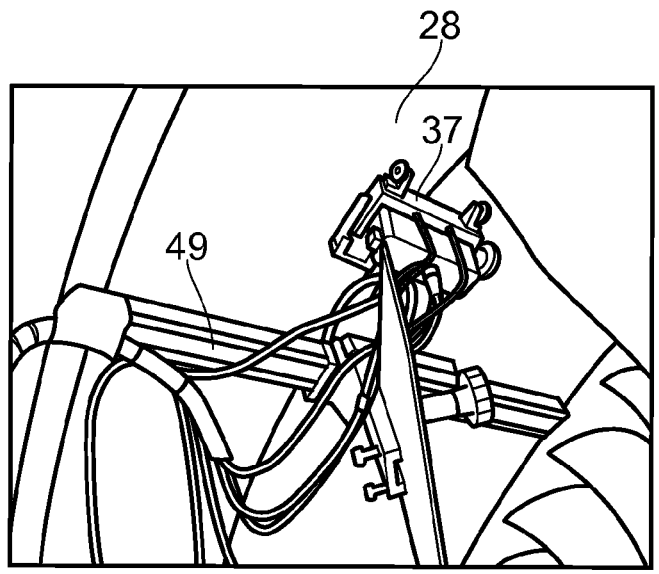
FIG. 10 is a view corresponding generally to that of FIG. 9, showing part of the assembly in a further alternate position relative to the fan track liner during scanning of a final region of the fan track liner.

Following an initial scan around the forward region of the fan track liner 28 as described above, the chassis 37 of the test assembly 32 is moved axially rearwardly, as illustrated in FIG. 8, ready for another circumferential scan of the fan track liner 28 to capture data relating to a second axial region of the liner. This may be achieved by sliding the slide carriage 47 rearwardly along the slide track 49 as illustrated, and then locking it in position via the second knob 50. The encoder 51 will then provide data to the computer which is indicative of the axial position of the chassis 37, and hence also the transducer probe 34, relative to the fan track liner 28. The fan 12 is then rotated again, in the same manner as described above, to scan the transducer probe 34 across the full circumference of the fan track liner 28. The above-mentioned steps may then be repeated to scan the entire extent of the fan track liner 28 in axial increments, as depicted in FIGS. 9 and 10.

As will be appreciated, the above-described method provides a convenient way to inspect the fan track liner 28 of the engine 10 for structural anomalies which does not require removal of the fan 12 from the engine, and which systematically and reliably scans the entire fan track liner 28 in a manner effective to provide recordable data representative of the condition and structural integrity of the fan track liner 28.

Figure 11:
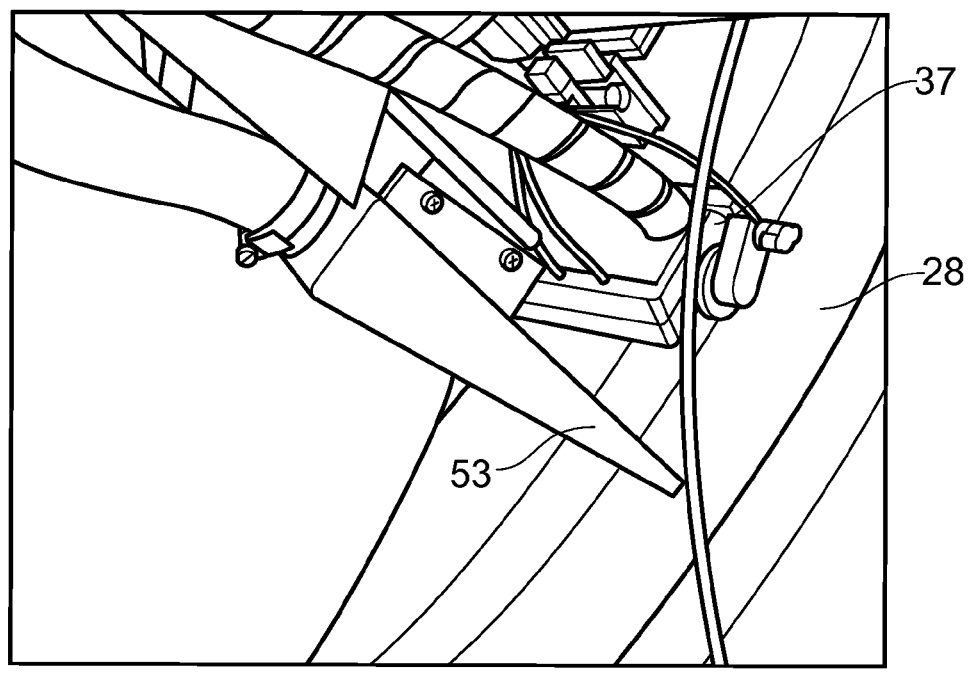
FIG. 11 is a perspective view of part of a test assembly in accordance with another embodiment of the disclosure, comprising a vacuum nozzle.

Whilst the invention has been described above with reference to a specific embodiment, it is to be appreciated that various changes and modifications can be made to the method without departing from the scope of the claimed invention. For example, the testing assembly 32 could be modified by the provision of a vacuum assembly in order to collect surplus couplant liquid during the scanning process, in order to prevent the liquid pooling in the lower region of the fan case of the engine. FIG. 11 illustrates a possible modification of this sort, in which the testing assembly 32 includes a vacuum nozzle 53 which is mounted so as to adopt a position adjacent the chassis 37 supporting the transducer 37. The nozzle 53 is fluidly connected to a vacuum pump arrangement (not shown) which is operable during rotation of the fan 12 to suck up the liquid couplant from the region of the chassis 37 after it has been directed between the couplant material 38 and the fan track liner 28.

It is also envisaged that in variants of the method proposed above, the test-blade 32 could be replaced by an elongate support of a configuration which is different to the fan blades 25 of the fan 12. For example, a simple elongate arm could be used instead of the test-blade, the arm being engaged at one end with the hub 24 of the fan in place of the removed fan blade 25, and extending generally radially between the two neighbouring fan blades to support the test assembly 32 at its radially outermost end.

It is also possible to use a separate emitter and receiver as the inspecting device instead of a transducer 34 as such. In such an arrangement both the emitter and the receiver could be mounted to the fan 12. Alternatively, only the emitter could be mounted to the fan, with the received mounted at another convenient position on the engine, or vice-versa.

When used in this specification and claims, the terms "comprises" and "comprising" and variations thereof mean that the specified features, steps or integers are included. The terms are not to be interpreted to exclude the presence of other features, steps or integers.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A method of inspecting a fan track liner of a gas turbine engine of a type having a rotatable propulsive fan circumscribed by the fan track liner and having a plurality of fan blades extending radially outwardly from a central hub, the method comprising the steps of:
    affixing at least part of an inspecting device to the fan so as to be directed towards the fan track liner; and
    rotating the fan within the fan track liner to move said at least part of the inspecting device circumferentially relative to at least a region of the fan track liner to thereby scan said region of the fan track liner with said at least part of the inspecting device, wherein
    said inspecting device comprises an ultrasonic transducer which is affixed to said fan,
    said ultrasonic transducer is provided within an assembly which, when affixed to said fan, is supported in sliding contact with a radially innermost surface of the fan track liner during the or each said step of rotating the fan, and
    said assembly comprises an ultrasonic couplant material arranged between the ultrasonic transducer and the fan track liner and for sliding contact with the fan track liner during the or each said step of rotating the fan to facilitate transmission of ultrasonic energy from the ultrasonic transducer into the fan track liner,
    said step of affixing at least part of the inspecting device to the fan involves positioning said at least part of the inspecting device adjacent the fan track liner, such that said step of rotating the fan is effective to move said at least part of the inspecting device across a radially innermost surface of the fan track liner, and
    wherein said method further comprises a step of directing an ultrasonic couplant liquid between the ultrasonic transducer and the fan track liner during the or said each step of rotating the fan.

2. A method according to claim 1, performed without removing the fan from the engine such that said step of rotating the fan is performed with the fan in the fan's normal position within the engine.

3. A method according to claim 1, wherein said step of rotating the fan is performed manually by hand.

4. A method according to claim 1, in which said step of rotating the fan involves rotating the fan through at least 360 degrees to thereby scan an entire circumference of said at least a region of the fan track liner with said at least part of the inspecting device.

5. A method according to claim 1, further including the steps of: adjusting an axial position of said at least part of the inspecting device affixed to the fan relative to said fan track liner after said step of rotating the fan, and then repeating said step of rotating the fan to move said at least part of the inspecting device circumferentially relative to a further region of the fan track liner, thereby scanning said further region of the fan track liner with said at least part of the inspecting device.

6. A method according to claim 5, wherein said steps of adjusting the axial position of said at least part of the inspecting device affixed to the fan relative to said fan track liner and rotating the fan are repeated a plurality of times to scan the fan track liner in a plurality of axial increments.

7. A method according to claim 1, including the steps of: removing a fan blade from the fan; and replacing said removed fan blade with a support extending radially outwardly from a hub of the fan and which supports said at least part of the inspecting device adjacent the fan track liner.

8. A method according to claim 7 in which only a single said fan blade is removed from the fan.

9. A method according to claim 7, in which said support is provided in the form of a designated test-blade of similar form to the fan blade of the fan.

10. A method according to claim 9, in which said test-blade is shorter in the radial direction than the fan blades forming the fan, and has an assembly comprising said at least part of the inspecting device mounted to a radially outermost region of the assembly.

11. A method according to claim 1, wherein said inspecting device comprises first and second elements, at least one of said elements being affixed to the fan.

12. A method according to claim 11, wherein said first element is a receiver and said second element is an emitter.

13. A method according to claim 1, including the steps of: removing a fan blade from the fan; and replacing said removed fan blade with a support extending radially outwardly from a hub of the fan and which supports said at least part of the inspecting device adjacent the fan track liner, and wherein said assembly is supported for axial movement relative to said support.

14. A method according to claim 1, wherein said assembly is radially outwardly biased towards the fan track liner.

15. A method according to claim 1, wherein the radially innermost surface of the fan track liner is in rubbing contact with radially outermost tips of the fan blades.

* * * * *